United States Patent [19]

Groth et al.

[11] Patent Number: 5,543,490

[45] Date of Patent: *Aug. 6, 1996

[54] PROCESS FOR THE PREPARATION OF POLYSUCCINIMIDE, POLYASPARTIC ACID AND SALTS THEREOF, AND THE USE OF THESE COMPOUNDS

[75] Inventors: Torsten Groth, Reinbek; Winfried Joentgen, Köln; Hans W. Linden, Odenthal; Nikolaus Müller, Monheim; Heinz-Joachim Rother, Krefeld; Paul Wagner, Düsseldorf; Martin Kugler, Leichlingen, all of Germany

[73] Assignee: Bayer AG, Leverkusen, Germany

[*] Notice: The term of this patent shall not extend beyond the expiration date of Pat. No. 5,493,004.

[21] Appl. No.: 168,847

[22] Filed: Dec. 17, 1993

[30] Foreign Application Priority Data

Dec. 24, 1992 [DE] Germany .................... 42 44 031.9

[51] Int. Cl.⁶ ........................................ C08G 69/00
[52] U.S. Cl. .................. 528/328; 528/361; 528/363; 528/367; 525/419; 525/420; 525/421; 525/539
[58] Field of Search ................... 528/328, 363, 528/361, 367; 525/420, 539, 419, 421

[56] References Cited

U.S. PATENT DOCUMENTS

| | | | |
|---|---|---|---|
| 3,846,380 | 11/1974 | Fujimoto et al. | 528/335 |
| 4,590,260 | 5/1986 | Harada et al. | 528/328 |
| 4,696,981 | 9/1987 | Harada et al. | 525/328 |
| 4,839,461 | 6/1989 | Boehmke | 528/328 |
| 5,057,597 | 10/1991 | Koskan | 528/328 |
| 5,142,062 | 8/1992 | Knebel et al. | 548/545 |
| 5,219,952 | 6/1993 | Koskan et al. | 525/419 |
| 5,221,733 | 6/1993 | Koskan et al. | 530/333 |
| 5,288,783 | 2/1994 | Wood | 525/418 |
| 5,296,578 | 3/1994 | Koskan et al. | 528/363 |
| 5,328,631 | 7/1994 | Du Vosel et al. | 252/174.23 |
| 5,393,868 | 2/1995 | Freeman et al. | 528/480 |

FOREIGN PATENT DOCUMENTS

| | | |
|---|---|---|
| 0578448 | 1/1994 | European Pat. Off. . |
| 0593187 | 4/1994 | European Pat. Off. . |
| 2246786 | 2/1992 | United Kingdom . |
| WO92/14753 | 9/1992 | WIPO . |
| WO93/23452 | 11/1993 | WIPO . |

OTHER PUBLICATIONS

Kovacs et al., J. Org. Chem. 26, 1084 (1961). The month of publication is not available.

Dessaignes, Compt. Rend. XXXI, 432–433 (1850). The month of publication is not available.

Harada, Polycondensation of Thermal Precursors of Aspartic Acid, Journal of Org. Chem., vol. 24 pp. 1662–1666 (1959). The month of publication is not available.

Chemical Abstracts, vol. 111, No. 6, 7 Aug. 1989, Columbus, Ohio, US; abstract No. 40111d, *Zusammenfassung* & JP–A–63 270 735 (KOEI CHEMICAL) 8 Nov. 1988.

Dessaignes, Quarterly Journal of the Chemical Society of London, vol. III, reprinted 1950. Translation of Comp. Rend. XXX, 324. The month of publication is not available.

*Primary Examiner*—Shelley A. Dodson
*Assistant Examiner*—P. Hampton-Hightower
*Attorney, Agent, or Firm*—Connolly & Hutz

[57] ABSTRACT

Polyaspartic acid is prepared by reacting maleic anhydride and ammonia to give maleamic acid, polymerizing the maleamic acid and subsequently hydrolyzing the product to give polyaspartic acid or a salt thereof.

18 Claims, No Drawings

PROCESS FOR THE PREPARATION OF POLYSUCCINIMIDE, POLYASPARTIC ACID AND SALTS THEREOF, AND THE USE OF THESE COMPOUNDS

The invention relates to a process for the preparation of polysuccinimide and polyaspartic acid and salts thereof by reaction of maleic anhydride derivatives, and to the use of these compounds.

The preparation and use of polyaspartic acid (PAA) and derivatives thereof have been described in numerous publications and patents going back some time. Thus, the preparation can be effected by thermal polycondensation of aspartic acid (J. Org. Chem. 26, 1084 (1961)).

U.S. Pat. No. 4,839,461 (=EP-A 0 256 366) describes the preparation of polyaspartic acid from maleic anhydride, water and ammonia. Maleic anhydride is converted into the monoammonium salt in aqueous medium with addition of concentrated ammonia solution. The monoammonium salt is polymerized in the melt to give Polysuccinimide. It is converted to polyaspartic acid or a salt thereof by hydrolysis.

U.S. Pat. No. 4,590,260 (=JP-A 1984(59)/60160) discloses the polycondensation of amino acids together with derivatives of malic, maleic and/or fumaric acid at from 100° to 225° C. U.S. Pat. No. 4,696,981 uses microwaves in these reactions.

DE-A 2 253 190 (=U.S. Pat. No. 3,846,380) describes a process for the preparation of polyamino acid derivatives, specifically polyaspartic acid derivatives. In addition to aspartic acid, this process uses maleic acid derivatives (monoammonium salt and monoamide, see examples) for the preparation of the intermediate polysuccinimide by thermal polymerization; the polysuccinimide can itself be converted into the desired derivatives by means of amines in suitable solvents.

The PAA can be employed, inter alia, as a scale inhibitor and scale deposit remover (U.S. Pat. No. 4,839,461, EP-A-256 366, U.S. Pat. No. 5,116,513). Other known applications are, for example, as a detergent additive or fertilizer (U.S. Pat. No. 4,839,461, EP-A-256 366, EP-A 454 126) and for the production of bone replacement materials (EP-A 383 568).

The invention relates to a process for the preparation of polysuccinimide and polyaspartic acid and salts thereof from maleamic acid, characterized in that maleic anhydride and ammonia are reacted, optionally in the presence of a solvent, to give maleamic acid, the maleamic acid is subjected to continuous thermal polymerization at from 100° C. to 350° C. in a reactor at a residence time of from 0.5 to 30 minutes, and the resultant polysuccinimide is, if desired, converted into polyaspartic acid or a salt thereof by hydrolysis.

The polysuccinimide produced according to the present invention contains in a preferred embodiment essentially recurring units of the following formula

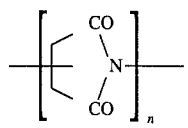

In the present invention, polyaspartic acid is taken to mean both free polyaspartic acid and salts thereof.

In a preferred embodiment, the polysuccinimide and the polyaspartic acid prepared according to the invention contain further recurring units of the following structure; depending on process conditions and educts:

a) aspartic acid units of the formula

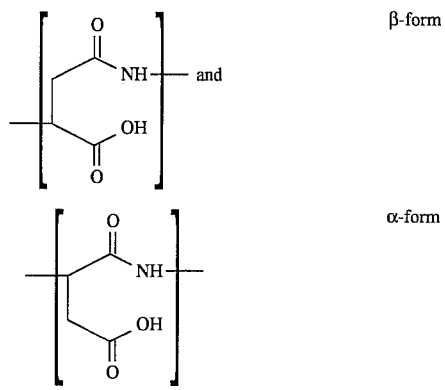

Generally at least 50%, especially at least 70% of the polyaspartic acid units are present in the β-form.

b) malic units of the formula

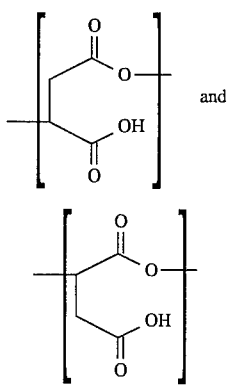

c) maleic and fumaric units of the formula

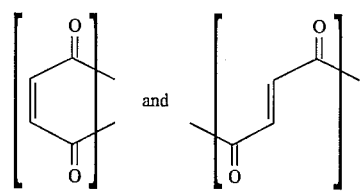

The recurring units b) and c) are preferably present in an amount of from 1:1 to 1:100, based on the total amount of a).

Analysis of the chemical structure is preferably carried out using $^{13}$C-NMR and, after total hydrolysis, by means of HPLC, GC and GC/MS.

The product obtained directly from polymerization or hydrolysis can contain the abovementioned recurring units a) and simultaneously the imide structures prepared with elimination of $H_2O$.

The polymerisation products can be converted into the corresponding salt of the polyaspartic acid by hydrolysis in a base at 20° to 95° C., especially 40° to 70° C., preferred at 50° to 70° C. Furthermore it is possible to obtain the free polyaspartic acid by hydrolysis in water at 80° C. to 100° C. or by treatment of the salt with acids or with acidic ion exchangers.

It is assumed that the following structures are intermediates in the reaction according to the invention:

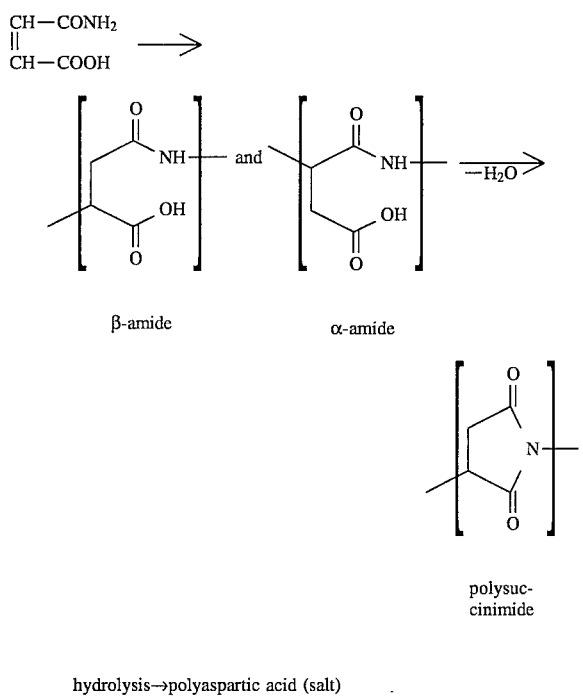

β-amide    α-amide polysuccinimide hydrolysis→polyaspartic acid (salt)

In a preferred embodiment of the invention, maleic anhydride and ammonia are reacted in an inert solvent to give maleamic acid. Particularly preferred solvents are halogenated and non-halogenated aromatic hydrocarbons, alkanes and ethers, such as, for example, chlorobenzene, o-dichlorobenzene, benzene, toluene, xylene, cumene, tetralin, methylene chloride, chloroform, diethyl ether, tetrahydrofuran, dioxane, dimethoxyethane, petroleum ether, hexane and heptane.

Examples of particularly preferred solvents are toluene, xylene, dichlorobenzene and o-dichlorobenzene. The reaction of the maleic anhydride with ammonia is carried out, in particular, at a pressure of from 0 to 10 bar, preferably at from 0 to 5 bar, in particular at from 0.5 to 3.5 bar, at a temperature of from 15° to 100° C., in particular at from 40° to 80° C., particularly preferably at from 60° to 70° C., and at a molar maleic anhydride:$NH_3$ ratio of from 1:0.8 to 1:1.5, preferably from 1:0.95 to 1:1.2, particularly 1:1.

In a particularly preferred embodiment of the invention, first maleic anhydride and ammonia are reacted with one another in an inert solvent (toluene) at from 60° to 70° C. and in the ratio 1:1. This forms a suspension of maleamic acid in the solvent in question. Removal of the solvent gives, without further purification, a maleamic acid in high purity and virtually quantitative yield. The preparation of maleamic acid has already been disclosed per se in JP-A 49/035 325, U.S. Pat. No. 2,459,964, DE-A 847 287 and DE-A 945 987.

The maleamic acid is converted into a polymerization product in a suitable continuous-operation reactor (paddle dryer, single-screw and twin-screw high-viscosity reactors, for example Discotherm and All-Phasen-Konti units from List, screw machines, preferably self-cleaning multiscrew machines or in a belt reactor) by continuous thermal rapid polymerization with a residence time of from 0.5 to 30 minutes, preferably from 1.5 to 15 minutes, at a temperature of from 100° to 350° C. (preferably from 155° to 230° C.), if desired in vacuo; the polymerization product can be converted into the corresponding polyaspartic acid salt by dissolution in a base at from 20° to 95° C., preferably at from 40° to 70° C., particularly preferably at from 50° to 70° C. It is also possible to obtain the free polyaspartic acid as early as this point by treatment with acids or acidic ion exchangers. The product is obtained as a fine powder by spray drying.

The above mentioned thermal polymerisation can otionally be carried out in the presence of a catalyst for example pyrosulphuric acid, phosphoric acid, sulphonic acid, phosphites, phosphonates or quaternary ammonium salts and the like.

The polymer prepared exhibits different chain lengths and molecular weights according to analysis by gel-permeation chromatography of $M_w$=500 to 10,000, preferably from 1000 to 5000, particularly preferably 2000 to 4000, depending on the reaction conditions, for example residence time and temperature of the thermal polymerization in the Konti reactor.

The invention furthermore relates to a process for the preparation of salts of the polyaspartic acid prepared according to the invention, in which the polysuccinimide or the free polyaspartic acid is reacted with bases. Examples of bases which can be used are alkali and alkaline earth metal hydroxides or carbonates, in particular NaOH, KOH or LiOH. The concentration of the base used is not crucial; it is preferably from 5 to 50% by weight in the form of aqueous solutions.

The compounds according to the invention are used, in particular, as dispersants, detergent additives, sequestrants, scale inhibitors, corrosion inhibitors, in particular for brass, and as microbicides and in fertilizers.

SPECIFIC EXAMPLES

1. Preparation of Maleamic Acid 4667 g of toluene dried by distillation and 1635 g=16.7 mol of maleic anhydride are introduced into a 10 l autoclave (V4A). The mixture is heated to 60° C. with stirring. After the mixture has been held at this temperature for 0.5 hour, 283 g=16.7 mol of dry $NH_3$ gas are introduced to a maximum pressure of 3 bar over the course of about 6 hours while the temperature is kept constant. When the calculated amount of $NH_3$ gas has been consumed, a residual pressure of 0.5 bar remains. The mixture is stirred at 60° c. for a further 2 hours and cooled to room temperature. The fine, milky white product suspension is filtered, giving 3933 g of filtrate and 2270 g of toluene-moist maleamic acid. Drying gives 1869 g of maleamic acid=97.5% of theory, melting point 168° C. The free-flowing product has a bulk density of 0.55 g/ml.

2. Preparation of Maleamic Acid (Concentrated Version in Order to Increase the Spacetime Yield and Efficiency)

3969 g of toluene dried by distillation and 2256 g=23.0 mol of maleic anhydride are introduced into a 10 l V4A autoclave. The mixture is heated to 60° C. with stirring. After 0.5 hour, 391 g=23.0 mol of dry $NH_3$ gas are introduced at from 60° to 70° C. and at a maximum pressure of 2.6 bar over the course of 4.5 hours. When the introduction is complete, the mixture is stirred for a further 2 hours. A residual pressure of about 0.5 bar remains. The reaction mixture is cooled to room temperature and filtered, giving 3305 g of toluene filtrate (the evaporation losses in the laboratory can be avoided in industry) and 2775 g of toluene-moist maleamic acid. Drying gives 2601 g of maleamic acid=93.2% of theory (yield based on carbon).

Melting point 165.2° C.

3. Preparation of Polysuccinimide (Polyimide Form)

14 kg of maleamic acid=121.7 mol (melting point: 166°–168° C., bulk density: 64.3 g/100 ml) were conveyed continuously from a feed hopper to the water-cooled part of a reactor screw by a conveying screw. At a mean residence time of from 1.5 to 5 minutes, the initially finely crystalline, white maleamic acid is conveyed into a prewarming zone at about 130° C. and then into the reaction zone at from about 155° to 185° C. A melt in which the polyaddition or polycondensation step takes place is formed in the reaction zone. The water of reaction formed (and any decomposition products) escape via a gas-emission tower.

The final part of the experimental apparatus (about ⅕ of the length) is closed, so that the water of reaction formed cannot escape at this point. The residual water therefore leaves the polymer composition emerging at the end of the screw in gas form, so that the high-viscosity substance expands with an (approximate) doubling in volume.

The rapidly cooling, beige, dry composition is powdered, giving 11,677 g of polymerization product. (Yield of 91.3% of theory, based on the carbon value).

4. Preparation of the Na Salt of Polyaspartic Acid, Spray-dried 11,246 g of the product obtained from 3)=107 mol (from carbon) are metered simultaneously with 8305 g of 48.8% strength NaOH=101.3 mol into 6620 g of $H_2O$ at from 50° to 60° C. A pH of 9 is not exceeded. During dissolution of the crude product, complete hydrolysis of the imide units without hydrolysis of the amide bonds of the polymer chain must take place. The approximately 50% strength solution prepared (density at 20° C.=1.342, pH=8.4) is spray-dried at evaporator temperatures of 80°/180° C. and a volume throughput of from 2 to 3 l/h). A finely pulverulent, pale-yellow powder is formed with a substance loss (through carbon analysis) of about 10%. The product can be employed directly as a sequestrant and dispersant and as a corrosion inhibitor.

14,605 g of PAA Na salt, spray-dried, are obtained.
Content: 31.7% by weight of carbon 5.7% by weight of water
Yield:90% of theory, from carbon It is also possible to use the aqueous aspartic acid Na salt solution directly without spray-drying.

FURTHER ANALYSES

1. Molecular Weight Determination by GPC

| $M_n$ | / | $M_w$ | / | $M_z$ |
|---|---|---|---|---|
| 1177 | / | 2569 | / | 3743 |

USE EXAMPLE

1. Test as Corrosion Inhibitor

Bare, degreased brass samples (MS 63) were used for the corrosion test. The test solution used was artificial seawater according to ASTM D 665-IP 135, to which the substance under test had been added. During the experimental period of 7 hours, the metal samples were fully immersed in the test solution at 55° C., into which about 100 ml/min of air were introduced.

After the test, the metal samples were cleaned for 15 seconds in semiconcentrated hydrochloric acid and washed with water and acetone. The dry metal samples were weighed before and after the test. The weight loss was used to calculate the percentage protective action S, based on a control sample:

$$S = \frac{m - m_1}{m} \times 100,$$

where
m=weight loss of the metal sample without inhibitor (control sample),
$m_1$=weight loss of the metal sample with inhibitor.

The results of the percentage protective action are shown in the table below:

| Concentration in mg/l | Protective action S in % |
|---|---|
| 10 | 9 |
| 25 | 70 |
| 50 | 81 |
| 0 | 0 |

2. Test for Antimicrobial Activity

The antimicrobial activity of the compounds according to the invention was analysed by determining the minimum inhibition concentration (MIC).

To this end, agar prepared from brewers wort and peptone was treated with the compound according to the invention in various concentrations. After the agar had solidified, it was contaminated with pure cultures of the test organisms shown in the table. After storage at 28° C. and relative atmospheric humidity of from 60 to 70% for 2 weeks, the MIC was determined. The MIC is the lowest concentration of active compound at which no colonization by the microbe species used takes place.

The table below shows the MIC values for the compound according to the invention.

| Test organism | MIC values in mg/l |
|---|---|
| *Bacillus subtilis* | 3000 |
| *Pseudomonas aeruginosa* | 3000 |
| *Penicillium brevicaule* | 3000 |
| *Chaetomium globosum* | 3000 |
| *Aspergillus niger* | 3000 |

3. Sequestration of a Surfactant

Assessment of the turbidity intensity of an alkylbenzenesulphonic acid Na salt solution in tap water.

1 ml of 10% strength Marlon A 375 solution is made up to 100 ml with tap water (total hardness 14.1 (German hardness)) with addition of 0.1 g of spray-dried PAA Na salt. The resultant solution has a stability of more than 7 days. Without addition of PAA Na salt, the solution becomes turbid in a few minutes.

4. Dispersion of Zinc Oxide a) 0.3 g of PAA Na salt are dispersed in 200 ml of tap water with 10 g of zinc oxide. The dispersion is introduced into a 250 ml measuring cylinder. After 3 hours, samples are taken from various points of the measuring cylinder and analysed for their zinc oxide content. It was found that the zinc oxide content is always the same as a consequence of the good dispersing action. Furthermore, the sedimentation stability is determined after 3 hours and after 24 hours. In both cases, virtually no sedimentation layer on the base of the measuring cylinder is observed.

We claim:

1. Process for the preparation of polysuccinimide, polyaspartic acid and salts thereof from maleamic acid, wherein maleic anhydride and ammonia are reacted, optionally in the presence of a solvent, to give maleamic acid, the maleamic acid is subjected to continuous thermal polymerization at from 100° C. to 350° C. in a reactor at a residence time of from 0.5 to 30 minutes, and the resultant polysuccinimide is, if desired, converted into polyaspartic acid or a salt thereof by hydrolysis.

2. Process for the preparation of polysuccinimide, polyaspartic acid and salts thereof from maleamic acid, characterized in that maleic anhydride and ammonia are reacted, optionally in the presence of a solvent, to give maleamic acid, the maleamic acid is subjected to continuous thermal polymerization at from 155° C. to 230° C. in a reactor at a residence time of from 1.5 to 15 minutes, and the resultant polysuccinimide is, if desired, converted into polyaspartic acid or a salt thereof by hydrolysis.

3. Process according to claim 1, wherein the molecular weight of the polyaspartic acid, determined by gel permeation chromatography with absolute calibration, is from 500 to 10,000.

4. Process according to claim 1, wherein the polyaspartic acid contains recurring units which, in the form of the free acid, conform to the following structure:

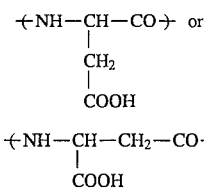

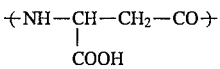

5. Process for the preparation of polyaspartic acid salts according to claim 1, wherein the polysuccinimide obtained according to claim 1 is hydrolyzed by means of a base.

6. Process according to claim 2, wherein the molecular weight of the polyaspartic acid, determined by gel permeation chromatography with absolute calibration, is from 500 to 10,000.

7. Process according to claim 2, wherein the polyaspartic acid contains recurring units which, in the form of the free acid, conform to the following structure:

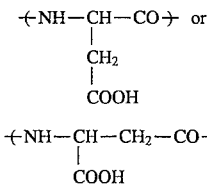

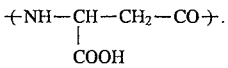

8. Process according to claim 3, wherein the polyaspartic acid contains recurring units which, in the form of the free acid, conform to the following structure:

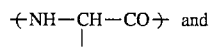

9. Process for the preparation of polyaspartic acid salts according to claim 2, wherein the polysuccinimide obtained according to claim 1 is hydrolyzed by means of a base.

10. Process for the preparation of polyaspartic acid salts according to claim 3, wherein the polysuccinimide obtained according to claim 1 is hydrolyzed by means of a base.

11. Process for the preparation of polyaspartic acid salts according to claim 4, wherein the polysuccinimide obtained according to claim 1 is hydrolyzed by means of a base.

12. Process for the preparation of polysuccinimide, polyaspartic acid and salts thereof from maleamic acid, wherein maleic anhydride and ammonia are reacted, in the presence of a solvent, to give maleamic acid, the maleamic acid is subjected to continuous thermal polymerization at from 100° C. to 350° C. in a reactor at a residence time of from 0.5 to 30 minutes, and the resultant polysuccinimide is, if desired, converted into polyaspartic acid or a salt thereof by hydrolysis.

13. Process according to claim 12, wherein the solvent is selected from the group consisting of halogenated aromatic hydrocarbons, non-halogenated aromatic hydrocarbons, halogenated alkanes, non-halogenated alkanes, halogenated ethers and non-halogenated ethers.

14. Process according to claim 12, wherein the solvent is selected from the group consisting of chlorobenzene, o-dichlorobenzene, benzene, toluene, xylene, cumene, tetralin, methylene chloride, chloroform, diethyl ether, tetrahydrofuran, dioxane, dimethoxyethane, petroleum ether, hexane and heptane.

15. Process for the preparation of polysuccinimide, polyaspartic acid and salts thereof from maleamic acid, wherein maleic anhydride and ammonia are reacted, in the presence of a solvent, to give maleamic acid, the maleamic acid is subjected to continuous thermal polymerization at from 155° C. to 230° C. in a reactor at a residence time of from 1.5 to 15 minutes, and the resultant polysuccinimide is, if desired, converted into polyaspartic acid or a salt thereof by hydrolysis.

16. Process according to claim 14, wherein the solvent is selected from the group consisting of halogenated aromatic hydrocarbons, non-halogenated aromatic hydrocarbons, halogenated alkanes, non-halogenated alkanes, halogenated ethers and non-halogenated ethers.

17. Process according to claim 14, wherein the solvent is selected from the group consisting of chlorobenzene, o-dichlorobenzene, benzene, toluene, xylene, cumene, tetralin, methylene chloride, chloroform, diethyl ether, tetrahydrofuran, dioxane, dimethoxyethane, petroleum ether, hexane and heptane.

18. Process according to claim 12, wherein the hydrolysis is effected by using a base selected from the group consisting of alkali earth metal hydroxides, alkali earth metal carbonates, alkaline earth metal hydroxides and alkaline earth metal carbonates.

* * * * *

UNITED STATES PATENT AND TRADEMARK OFFICE
CERTIFICATE OF CORRECTION

PATENT NO. : 5,543,490
DATED : August 6, 1996
INVENTOR(S) : Groth et al.

It is certified that error appears in the above-indentified patent and that said Letters Patent is hereby corrected as shown below:

In Column 7, lines 20-21 (Claim 2), "characterized in that" should be --wherein--.

In Column 8, line 1 (Claim 8), "and" should be --or--.

Signed and Sealed this

Thirty-first Day of December, 1996

Attest:

BRUCE LEHMAN

*Attesting Officer*      *Commissioner of Patents and Trademarks*